United States Patent
Girvin et al.

[11] Patent Number: 6,016,194
[45] Date of Patent: Jan. 18, 2000

[54] PARTICLES COUNTING APPARATUS AND METHOD HAVING IMPROVED PARTICLE SIZING RESOLUTION

[75] Inventors: Kenneth L. Girvin, Grants Pass; Richard K. DeFreez, Azalea, both of Oreg.

[73] Assignee: Pacific Scientific Instruments Company, Grants Pass, Oreg.

[21] Appl. No.: 09/113,986

[22] Filed: Jul. 10, 1998

[51] Int. Cl.[7] ............................. G01N 15/02; G01N 21/00
[52] U.S. Cl. ........................ 356/337; 356/335; 356/336; 356/338
[58] Field of Search ..................................... 356/336, 337, 356/338, 339, 340, 343, 345, 349; 250/222.2

[56] References Cited

U.S. PATENT DOCUMENTS

| | | | |
|---|---|---|---|
| 4,746,215 | 5/1988 | Gross | 356/339 |
| 4,896,048 | 1/1990 | Borden | 250/574 |
| 5,085,325 | 2/1992 | Jones et al. | 209/580 |
| 5,642,193 | 6/1997 | Girvin et al. | 356/339 |
| 5,726,753 | 3/1998 | Sandberg | 356/338 |

OTHER PUBLICATIONS

"Light Scattering Automatic Particle Counter", Japanese Industrial Standard, JIS B 9921, 1989, UDC 543.275.082.5:535.43:628.511.1, pp. 1–18.

*Primary Examiner*—Frank G. Font
*Assistant Examiner*—Michael P. Stafira
*Attorney, Agent, or Firm*—Stoel Rives LLP

[57] ABSTRACT

A particle counter (10) passes a sample stream of particles (72) through an elongated, flattened nozzle (16) and into a view volume (18) formed by an intersection of the sample stream and a laser beam (13). Scattered light (24) from the view volume is focused onto a linear array (32) of photo-diode detectors (40) positioned such that a longitudinal length (70) of the view volume is imaged on the detectors. Because the sample stream produces nonuniform particle velocities along the longitudinal dimension of the view volume, for same-sized particles higher velocity particles will generate lower output amplitude signals than lower velocity particles. Therefore, the gain associated with each photo-detector element is adjustable to compensate for the nozzle velocity differences, laser beam intensity differences caused by beam divergence and fluctuations, optical path efficiency variations, and photo-detector element-to-element sensitivity differences.

18 Claims, 4 Drawing Sheets

PARTICLES COUNTING APPARATUS AND METHOD HAVING IMPROVED PARTICLE SIZING RESOLUTION

TECHNICAL FIELD

The present invention relates to optical particle detection and, in particular, to a technique for improving particle sizing resolution by gain profiling an optical particle detector array.

BACKGROUND OF THE INVENTION

Contamination control, including particulate monitoring, plays a critical role in the manufacturing processes of several industries. These industries require clean rooms or clean zones with active air filtration and require the supply of clean raw materials such as process gases, deionized water, chemicals, and substrates. In the pharmaceutical industry, the Food and Drug Administration requires particulate monitoring because of the correlation between detected particles in an aseptic environment and viable particles that contaminate the product produced. Semiconductor fabrication companies require particulate monitoring as an active part of quality control. As integrated circuits become more compact, line widths decrease and wafer sizes increase such that the sizes of particulates causing quality problems become smaller. Accordingly, it is important to detect and accurately size submicron particles of ever decreasing sizes and numbers per volumetric unit.

To perform particulate monitoring, currently commercially available submicron particle sensors use optical detection techniques to determine the presence, size, and number of particles in a volumetric unit. The basic building block for this technology is intracavity optical scattering of a laser beam and detection of the optical signal scattered by the particles. The standard particle detection approach, which was developed during the late 1980s, passes a sample stream containing the particles through an elongated flattened nozzle such that the sample stream exiting the nozzle intersects the laser beam in an area referred to as a view volume. Scattered light from particles in the view volume is collected with optics and focused onto the detection system.

U.S. Pat. No. 5,642,193 for PARTICLE COUNTER EMPLOYING A SOLID-STATE LASER WITH AN INTRACAVITY VIEW VOLUME, which is assigned to the assignee of this application, describes such a particle detection and counting system along with techniques for improving particle sizing resolution. U.S. Pat. No. 4,746,215 for PARTICLE COUNTER AIR INLET ASSEMBLY describes a nozzle that produces a particle flow sample stream for developing a view volume in particle counting systems.

The nozzle, laser beam, and resulting view volume all have properties that affect particle detection sensitivity and sizing resolution. For example, the type of laser employed affects the laser beam lateral (transverse to the beam longitudinal axis) intensity profile, with prior art multispatial mode HeNe lasers typically having a "top-hat" shaped lateral intensity profile. Such lasers are used to provide sufficient intracavity optical power to produce detectable amounts of scattered light. To complement the laser beam top-hat intensity profile, the nozzles produced a turbulent flow having a substantially square lateral velocity profile where it intersects the laser beam. This is beneficial because the resulting view volume contains a top-hat lateral laser intensity profile and a complementary lateral particle velocity profile that together produce an overall uniform lateral particle detection sensitivity, which improves particle sizing resolution. Unfortunately, the turbulent nozzle flow produces intracavity noise in the view volume that degrades the particle detection signal-to-noise ratio. Reducing the nozzle flow rate to produce laminar flow results in a parabolic velocity profile that reduces intracavity noise, but also degrades particle sizing resolution and overall particle detection rate.

In addition to the above-described problems, the nozzles produce a sample stream longitudinal velocity profile that causes mono-disperse (uniformly distributed particles of the same size) particles to have different velocities depending on their longitudinal passage position through the view volume. Moreover, the laser beam intensity is not longitudinally constant along the view volume because of beam divergence and because the light collection optics cannot perfectly reproduce on the detection system image intensities generated in the view volume. Therefore, particle detection systems that detect light scattered from particles to produce pulse amplitudes indicative of particle size win, unfortunately, produce nonuniform output pulse amplitudes depending on the longitudinal positions of particles in the view volume.

What is needed, therefore, is a particle detection system having high, uniform particle detection sensitivity and sizing resolution throughout an entire view volume and, in particular, one that meets or exceeds the requirements set forth in JAPANESE INDUSTRIAL STANDARD JIS B 9921-1989 for a "Light Scattering Automatic Particle Counter."

SUMMARY OF THE INVENTION

An object of the invention is, therefore, to provide a particle detection method and system that is characterized by high submicron particle detection sensitivity and accurate particle size determination.

Another object of this invention is to provide a particle detection system that provides uniform detection sensitivity to laser light scattered from mono-disperse particles distributed anywhere throughout a view volume.

This invention preferably employs conventional particle detection techniques but may also be embodied in an optical scattering particle counter that uses a heterodyne detection technique.

A particle counter of this invention passes a sample stream containing the particles through an elongated, flattened nozzle and into a view volume formed by an intersection of the sample stream and a laser beam. The nozzle has a lateral dimension approximately equal to or less than the laser beam lateral dimension at the view volume and a longitudinal dimension ranging from about the lateral dimension to greater than about 20 times the lateral dimension. Scattered light from the view volume is collected with optics and focused onto the detection system. A linear photo-detector array is employed in the detection system and positioned such that the longitudinal dimension of the view volume is imaged on the linear array of photodetector elements. Because the sample stream produces nonuniform particle velocities along the longitudinal dimension of the view volume, for same-sized particles higher velocity particles will generate lower output amplitude signals than lower velocity particles. In this invention, however, the gain associated with each photo-detector element is adjusted to compensate for nozzle longitudinal dimension-related velocity differences, laser beam intensity differences caused by beam divergence, optical path efficiency variations, and photo-detector element-to-element sensitivity differences.

The process of adjusting the gains is referred to as normalization. To normalize the system, mono-disperse particles of a predetermined size are injected into the sample stream and into the view volume. The gain of each photo-detector amplifier is adjusted such that the output pulse amplitudes are substantially uniform for each photo-detector element in the array. After normalization the particle detector system is characterized by high submicron particle detection sensitivity and accurate particle size determination for particles distributed anywhere throughout the view volume.

In an alternative embodiment, particle sizing resolution is further improved by placing a light detector proximal to the laser beam to generate a signal indicative of laser beam intensity fluctuations. The signal is inserted into the gain normalization system to cancel out scattered light intensity fluctuations caused by the laser intensity fluctuations and detected by the array of photo-detector elements.

Additional objects and advantages of this invention will be apparent from the following detailed description of preferred embodiments thereof, which proceeds with reference to the accompanying drawings.

DETAILED DESCRIPTION OF PREFERRED EMBODIMNTS

Figure 1:
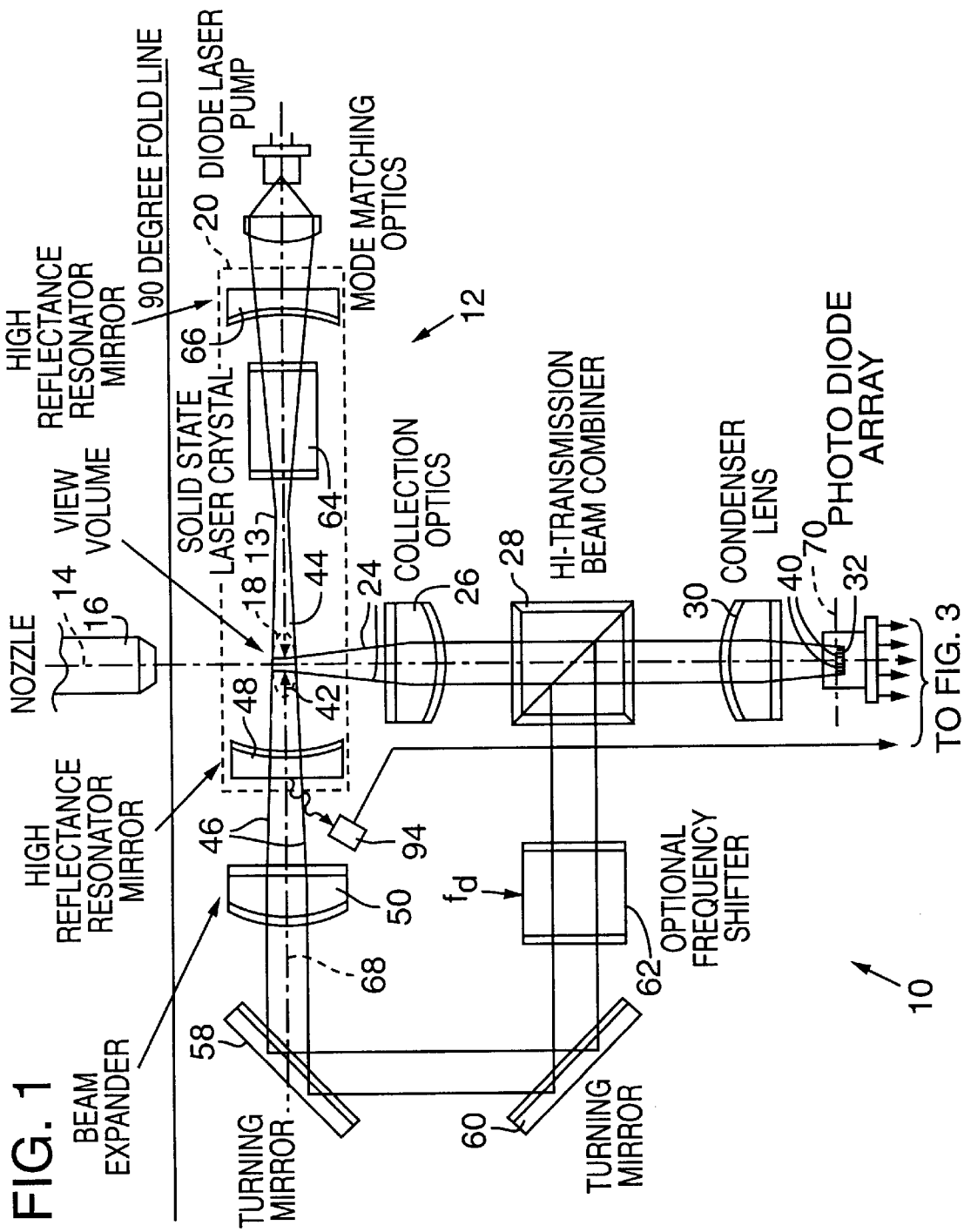
FIG. 1 is a block diagram of a high sensitivity airborne particle counter employing a photo-detector array gain normalization system of this invention.

FIG. 1 shows an airborne particle counter 10 that performs heterodyne detection of small particles as described in copending U.S. patent application Ser. No. 09/032,257, filed Feb. 27, 1998, for HETERODYNE OPTICAL PARTICLE DETECTION TECHNIQUE, which is assigned to the assignee of this application. Although this invention preferably employs conventional particle detection techniques, which are a subset of particle counter 10, this invention may also employ heterodyne detection techniques. Particle counter 10 includes a diode laser-pumped, high intracavity intensity solid-state laser 12, which is robust, efficient, and compact; operates in the absence of high voltages; and can be constructed to have the high beam intensity and spectral qualities required for efficient heterodyne detection. (The invention could also be practiced with gas or dye lasers.) Laser 12 generates a laser beam 13 having an intracavity optical intensity that scatters radiation from particles injected in a flow direction 14 by an elongated, flattened nozzle 16 within a view volume 18 in a resonator 20 of laser 12. Scattered light rays 24 are collected and collimated by collection optics 26, transmitted through a beam combiner 28, and then imaged by a condenser lens 30 onto a linear array 32 of photodiode detectors 40. Each photodiode detector 40 of array 32 detects the scattered light rays 24 from a longitudinal portion 42 surrounding a laser beam 13 having a longitudinal axis 44 in view volume 18. Nonscattered light rays 46 simultaneously leak out of a left-hand side resonator mirror 48 and are collected, expanded, and collimated by a beam expander 50. An expanded beam of nonscattered light rays 46 is then redirected by a pair of turning mirrors 58 and 60 to beam combiner 28 from which it collinearly copropagates to condenser lens 30 where it is focused onto linear array 32 of photodiode detectors 40.

The detection technique implemented by particle counter 10 is referred to as a self-heterodyne or "homodyne" detector because it uses the same optical oscillator to generate the signal (particle scattered light rays 24) and the local oscillator (nonscattered light rays 46). Heterodyne detection entails developing a beat frequency signal between the particle scattered light signal and the local oscillator in a square-law detector that is, in this case, photodiode detectors 40. The beat frequency is selectively detected to the exclusion of other beat frequencies. The beat frequency for self-heterodyne detection is at zero frequency, i.e., a DC signal, which is known to be a particularly undesirable detection frequency because of 1/f noise. Shifting the beat frequency to some nonzero value in accordance with what is called an offset heterodyne technique eliminates the 1/f noise problem. Offset heterodyne detection can be accomplished by direct frequency shifting by means of an optional frequency shifter 62. A suitable frequency shifter 62 is an acousto-optic modulator receiving a drive signal, $f_d$, that provides the offset frequency.

The intracavity modal structure required for heterodyne detection has quite different spatial properties from those of conventional high intracavity-intensity HeNe laser-based particle detectors. The latter lasers contain multilongitudinal spectral and multilateral spatial modes that result in temporal and spatial optical chaos (optical turbulence noise). Heterodyne detection uses single spectral and spatial mode performance for efficient operation. A preferred embodiment uses a high intracavity-intensity, lowest order Gaussian mode derived from a half-symmetric spherical mirror resonator (not shown).

Laser resonator 20 contains a Cr:LiSAF crystal 64 and curved resonator mirrors 48 and 66 with HR coatings ($R^{\sim}0.999965$) to provide high intensity in a fundamental Gaussian mode. This configuration reduces the number of optical elements and optical surfaces in resonator 20 and thus reduces round-trip scattering and absorption losses. Single longitudinal mode control for a Cr:LiSAF lasing medium may require use of a spectral narrowing element in resonator 20 or use of injection locking to compensate for an insufficient etalon effect of the Cr:LiSAF crystal.

Because heterodyne particle detection has increased sensitivity, nozzle flow rate can be reduced to produce a sample stream having laminar flow and, consequently, a Gaussian lateral velocity profile that complements the laser beam Gaussian intensity profile. Accordingly, particle counter 10 is suitable for detecting particles having sizes ranging from about 0.025 microns to about 25 microns at carrier gas flow rates ranging from about 0.1 cubic feet per minute ("cfin") to about 2.0 cfm.

Figure 2:
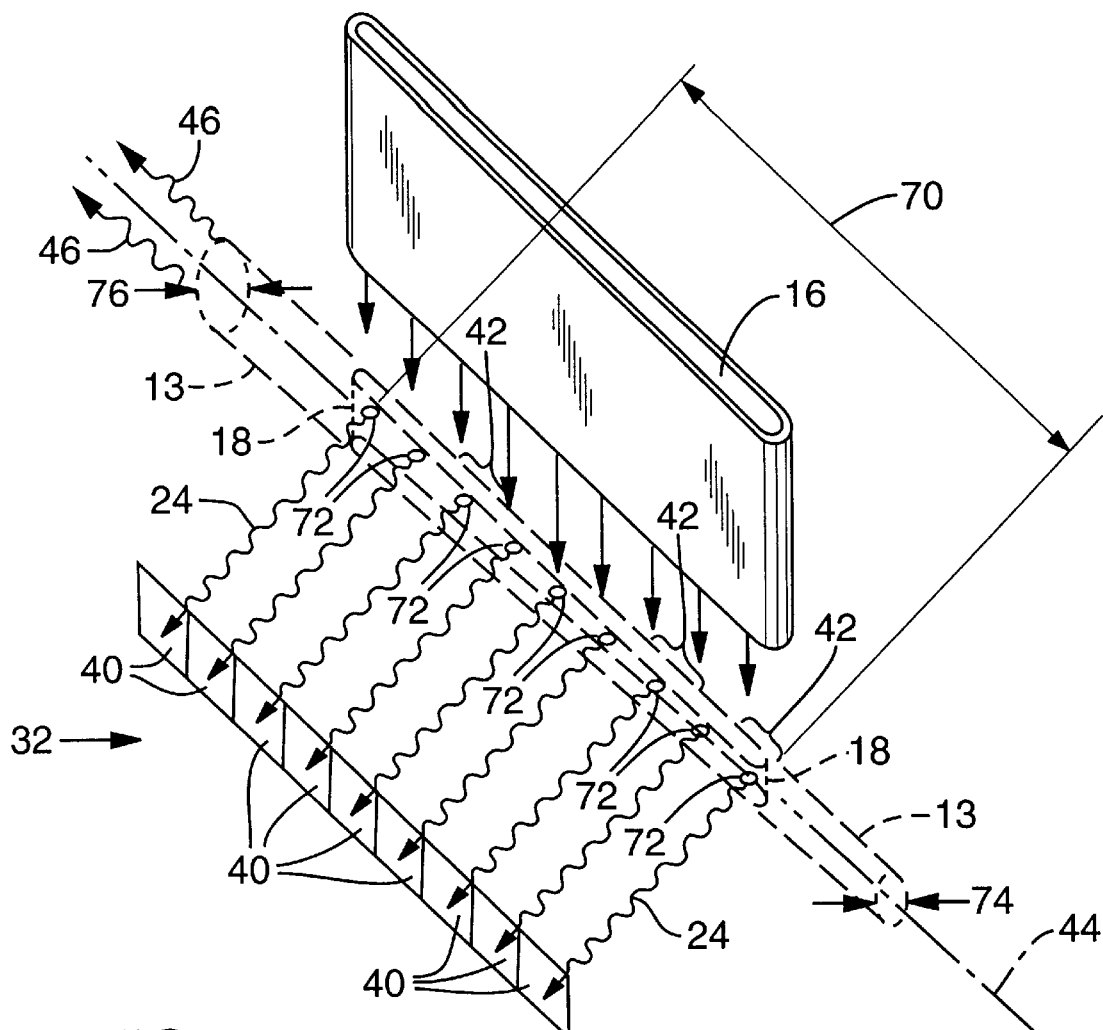
FIG. 2 is an enlarged isometric pictorial representation of a radiation beam, a nozzle, and a photo-detector array sensing particles in a view volume of this invention.

Referring also to FIG. 2, particle counter 10 is preferably designed for high detection efficiency across a wide range of carrier gas flow rates. The efficiency of a heterodyne detection system is inversely proportional to its angular field of view. This is true because the optical heterodyne efficiency is inversely proportional to the integral of the phase difference between the local oscillator field and scattered signal wavefronts over the surface of a photodiode detector 40. In short, large detectors lead to larger integrals or lower intensity heterodyne signals. On the other hand, the flow rate of intracavity particle counter 10 is proportional to a longitudinal length 70 of view volume 18. Because particle counter 10 employs a linear array 32 of photodiode detectors 40, many parallel heterodyne detection channels are created, which allow for a relatively long longitudinal length 70 of view volume 18 while maintaining the efficiency of the heterodyne detection system.

The heterodyne detection system uses linear array 32 of photodiode detectors 40 having dimensions that are proportional to the image dimensions of view volume 18. Linear array 32 is arranged such that scattered light from each particle 72 passing through view volume 18 is imaged (optics not shown in FIG. 2) onto the one detector 40 corresponding to that area of view volume 18. The height of each detector 40 is proportional to the distance the particle travels laterally through view volume 18, and the length of linear array 32 is proportional to longitudinal length 70 of view volume 18. The width of each detector 40, and the gap between them, is minimized to provide increased phase overlap between particle scattered light rays 24 and nonscattered light rays 46 and to lower the detector capacitance.

The heterodyne detection system works well for the majority of particles 72 ejected from nozzle 16, which is preferably implemented as described in U.S. Pat. No. 4,746,215 for PARTICLE COUNTER AIR INLET ASSEMBLY. The system produces relatively good particle sizing resolution at nozzle 16 carrier gas flow rates of about 0.1 cfm. However, particle sizing resolution needs improvement, especially at higher carrier gas flow rates, such as 1.0 cfm to 2.0 cfm.

Particle sizing resolution depends on each of detectors 40 generating pulses that accurately represent the sizes of particles 72. However, detectors 40 integrate received photons to generate ramped pulses having magnitudes (amplitude times pulse duration) that are proportional to the time it takes particles 72 to traverse view volume 18, the sizes of particles 72, the intensity of laser beam 13, and the sensitivity of each detector 40. Unfortunately, nozzle 16 produces a sample stream velocity profile that causes particles 72 to have different velocities (shown as various length vectors exiting nozzle 16) depending on their longitudinal passage position through view volume 18. Also, the intensity of laser beam 13 is not longitudinally constant along the view volume because of beam divergence (shown as a difference in laser beam 13 waist diameters 74 and 76). Moreover, the sensitivities of detectors 40 are typically nonuniform across linear array 32 because the light collection optics nonuniformly image on detector 40 light scattered from view volume 18.

Because nozzle 16 produces nonuniform particle velocities along longitudinal length 70 of view volume 18, for equally sized particles 72, higher velocity particles have a lesser time in view volume 18 and, therefore, cause detectors 40 to generate lower magnitude output signals than lower velocity particles. In this invention, however, the gain associated with each of detectors 40 is adjustable to compensate for nozzle 16 longitudinal dimension-related velocity differences, laser beam 13 intensity differences, optical path efficiency variations, and linear array 32 detector-to-detector sensitivity differences so that the detector signal magnitudes accurately represent the sizes of particles 72. Of course, the sensitivity differences may, in part, be attributed to optical path light transmission variations.

One way of achieving gain uniformity in a linear array light detector application is described in U.S. Pat. No. 5,085,325 for COLOR SORTING SYSTEM AND METHOD, in which a line scanning video camera views agricultural articles moving on a conveyor belt and generates brightness and color corrected images that are processed to differentiate acceptable from unacceptable articles. Gain correction scaling is accomplished using digital signal processing techniques to compensate for conveyor belt lighting, optical path, and detector-to-detector sensitivity variations. However, all the articles are moved by the conveyor belt at the same speed, lighting intensity fluctuations are not accounted for, and the articles are many orders of magnitude larger than the submicron sized particles detected by particle counter 10. Clearly, different detection sensitivities and gain correction factors must be employed in submicron particle detection than those used in agricultural product inspection applications.

Figure 3:
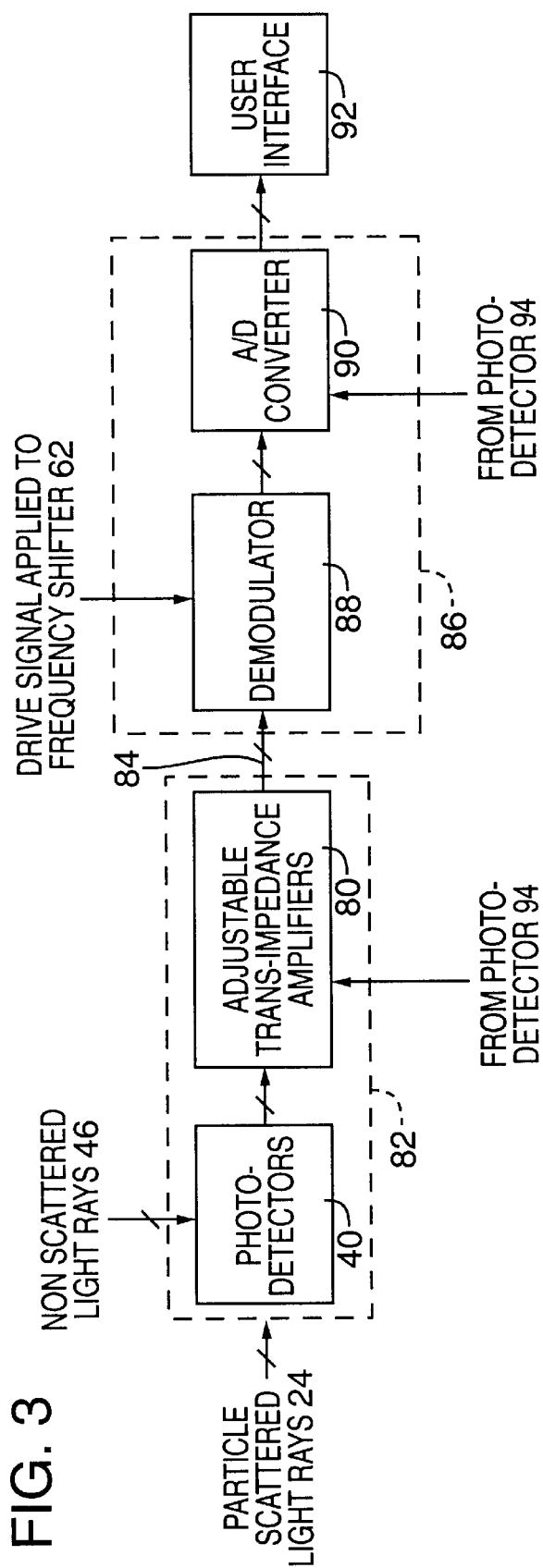
FIG. 3 is a block diagram showing the processing of signals derived from particle scattered light rays in accordance with the gain normalization technique of this invention.

FIG. 3 shows in block diagram form the processing of signals derived from particle scattered light rays 24 and nonscattered light rays 46. In a parallel detection embodiment, each detector 40 is connected to an adjustable-gain trans-impedance amplifier 80 to form a gain normalized photo-amplifier 82. Each trans-impedance amplifier 80 is adjusted (calibrated) by injecting mono-disperse particles 72 of a predetermined size into view volume 18 and changing the gain and/or frequency response (or integration time) of each trans-impedance amplifier 80 such that all of their output magnitudes are substantially equal.

Producing a calibration carrier gas flow containing mono-disperse particles first entails purchasing poly-styrene-latex ("PSL") spheres from a manufacturer such as Duke Scientific of Palo Alto, Calif. The PSL spheres have a traceable size corresponding to standards maintained by the National Institute of Standards and Technology. Several different sizes of PSL spheres are available with each size having a size variance of about ±3%. PSL spheres of one of a selected one of the sizes are suspended in a liquid containing a surfactant, which is diluted with deionized water ("DI"). The DI-PSL solution is ejected from an atomizer that disperses the particles into an aerosol. The atomizer produces the aerosol using pressurized air that is passed through a filter with retention down to 0.003 microns. The aerosol is then dried, neutralized, and passed through a Differential Mobility Analyzer ("DMA"). The DMA classifies the particles by size sending through only those that have an attached charge corresponding to a predetermined size with about a ±1% size variance. The DMA output is diluted with clean air passed through a 0.003 micron filter. The classified diluted mono-disperse PSL spheres are then sent to a Condensation Nucleus Counter ("CNC") and the particle counter being calibrated. The DMA size selection is adjusted to find the peak number of particles passing as measured with the CNC, which has a sensitivity of better than 0.010 microns and about a 100% counting efficiency at 0.050 microns (as verified by the University of Missouri at Rolla). The CNC and particle counter have flow meters attached to ensure a constant flow rate. The output of the particle counter being calibrated is sent to a Multi-Channel-Analyzer that measures the pulse amplitude of each output pulse. The pulse amplitude is directly proportional to the size of the particle, and the number of pulses represent the number of particles. Other particle sizes are subsequently passed through the system and their pulse heights are measured. The pulse height versus each particle size is plotted on a calibration curve. Additional information regarding particle counter calibration is described in the JIS B 9921-1989 standard.

When detecting particles 72 of predetermined or undetermined sizes, each detector 40 receives two optical carriers, one from particle scattered light rays 24 and one from nonscattered light rays 46. The combined light, in the case of the "offset heterodyne" technique, has a DC magnitude and a dominant beat frequency. The particle-scattered light carrier then becomes directly amplitude modulated as a particle traverses the laser beam. The resulting amplitude modulation of the dominant beat frequency contains particle sizing information. Each gain-normalized photo-amplifier output 84 is post-processed by processing circuitry 86, which includes demodulation electronics 88 and an analog-to-digital converter 90, to extract the signal amplitude representing the particle scattered light. The drive signal, $f_d$, applied to frequency shifter 62 to provide the offset frequency is used by demodulation electronics 88 to tune in the resulting optical carrier beat frequency. Analog-to-digital converter 90 converts the extracted analog signals to digital signals. The signal amplitude of the extracted signal represents the size of the particle. Repetitive signals represent the number of particles.

The resulting signals are directed to a user interface 92, as is typically done in conventional particle counters. The digital signals represent the size and number of the particles that pass through view volume 18.

In an alternative parallel embodiment, trans-impedance amplifiers 80 all have a substantially equal gain. However, the signals generated by each of trans-impedance amplifiers 80 are conveyed to a comparator having a threshold adjusted to trigger on the corresponding signal magnitude resulting from injecting mono-disperse particles 72 of a predetermined size into view volume 18. The threshold adjustment may be automated by employing analog-to-digital converters and programmable thresholds.

In conventional scattered light detection systems, the relationship of particle size to optical size is proportional to $d^6$, where d is the particle diameter. These detection systems have limits to the dynamic range of their output. The particle size to signal relationship in heterodyne detection is proportional to $d^3$. Therefore, heterodyne detection has the added advantage of increasing by a power of two the dynamic range of particle size detection.

Referring again to FIGS. 1 and 2, particle 72 sizing resolution can be further improved by positioning a photo-detector 94 to sample laser beam 13. When using a single mode laser 12, photo-detector 94 preferably samples laser beam 13 exiting from the left-hand side of resonator mirror 48. Photo-detector 94 generates a signal indicative of the intensity fluctuations of laser beam 13. The signal is conveyed to trans-impedance amplifiers 80 (if their gain is voltage-adjustable) or to analog-to-digital converter 90 (if its scale factor is voltage-adjustable) to divide out laser beam intensity fluctuations sensed by detectors 40. The signal may, alternatively, be conveyed to serial data normalization circuitry as described below.

In an alternative embodiment, linear array 32 is a serial readout charge-coupled-device array in which the signals from detectors 40 are serially digitized and processed through a lookup table containing multiplication factors representing corrections for nozzle 16 longitudinal dimension-related velocity differences, laser beam 13 intensity differences, and linear array 32 detector-to-detector sensitivity differences.

The lookup table multiplication factors are generated when, as in the above-described parallel implementation, mono-disperse, predetermined sized particles are injected during calibration of particle counter 10. An optional automated calibration process entails scanning the serial output of linear array 32 to determine the particular multiplication factor for each of detectors 40 to achieve a substantially uniform set of detector 40 signal magnitudes. The resulting multiplication factors are stored in a memory.

When particle counter 10 is subsequently used for detecting particles having undetermined sizes, each serial readout scan of linear array 32 is digitized and the digitized signal magnitudes for each of detectors 40 is scaled by its associated multiplication factor to accurately represent the sizes of particles 72.

To further improve particle sizing resolution in the linear array 32 serial readout embodiment, the photo-detector 94 signal indicative of laser beam 13 intensity fluctuations is digitized concurrently with each readout scan of linear array 32. The resulting laser intensity fluctuation data are stored in memory storage locations associated with the data from each of detectors 40 such that the data in each storage location represent the instantaneous laser beam 13 intensity level at the time each associated detector 40 was read out and digitized.

For example, linear array 32 may include an array of 512 detectors 40, and a memory stores 512 associated digitized magnitude values in a first set of 512 storage locations. During the same detector 40 readout period, 512 laser beam 13 intensity fluctuation values are stored in a second set of 512 storage locations. An overall corrected set of detector 40 data are achieved by first scaling the digitized signal magnitudes for each of detectors 40 by their associated multiplication factors and then correcting the scaled magnitudes by the associated laser beam intensity fluctuation data.

Any of the above-described linear array particle detection techniques is further advantageous because particle coincidence loss is reduced. Particle coincidence loss and sizing resolution are impaired in conventional single detector particle counters because of the increased chance that two or more particles may be detected at the same time. The resulting single detector signal magnitude is a summation of the two particle signals, which is erroneously counted as a single larger particle.

However, in another embodiment of a linear array-based particle detection system, particle sizing resolution can be further improved by summing the outputs of adjacent detectors 40 to recover particle scattered light that is simultaneously imaged on more than one detector. Adjacent output summing is particularly beneficial when the particle is imaged between adjacent detectors or is imaged across more than two detectors. In such instances, each detector 40 generates a reduced signal magnitude because only a portion of the scattered light is imaged thereon.

The optimal number of adjacent summed detectors is determined by comparing the image spot size produced by the collection optics to the number of detectors 40 that the image spot size covers. For example, if each detector 40 has a 200 micron width and the image spot size also has a 200 micron width, then the particle could potentially be imaged across two detectors. However, if the spot size has a 300 micron width, then the particle could potentially be imaged across three detectors 40.

Figure 4:
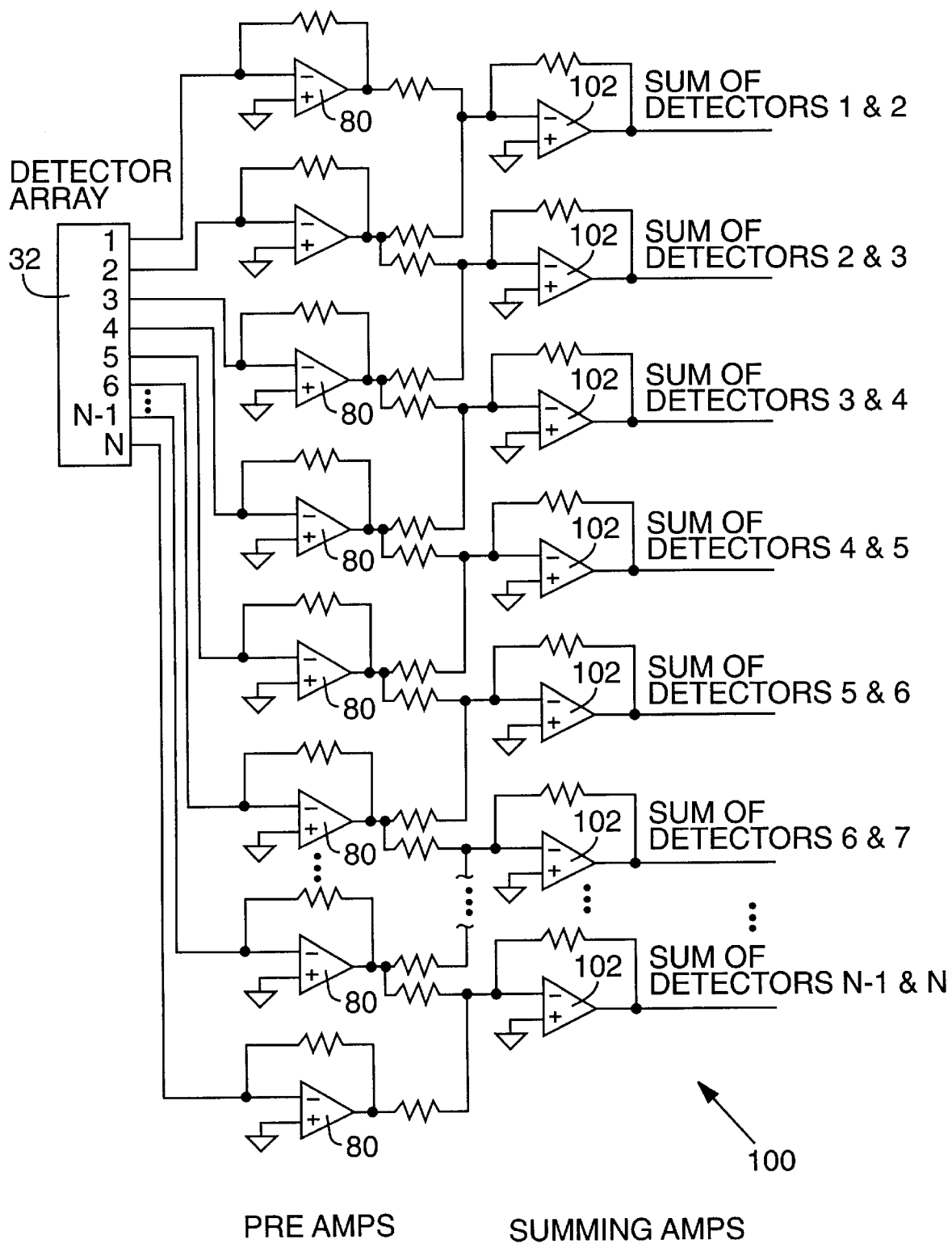
FIG. 4 is a schematic electrical circuit diagram of a detector array summing system of this invention.

FIG. 4 shows a preferred embodiment of a detector array summing system 100 that sums only adjacent pairs of detectors 40. In linear array 32, detectors 40 are arranged in a linear set of elements numbered sequentially from element 1 at one end, through elements 2, 3, 4, . . . and N−1, to element N at the opposite end. Each of elements 1 to N is electrically connected to an associated trans-impedance amplifier 80, adjacent outputs of which are summed by a set of summing amplifiers 102 to provide a set of output signals representing the sum of signal magnitudes from elements 1 and 2, 2 and 3, 3 and 4, . . . to N–1 and N. The resulting summed outputs are processed as described above with reference to FIG. 3. This arrangement ensures recovering from a particle image that overlaps adjacent detectors a signal indicative of accurate particle size.

A trans-impedance amplifier 80 particle image signal that is inadvertently summed with an adjacent trans-impedance amplifier nonparticle image signal will produce a signal having a lower magnitude. To preserve the coincidence loss advantage, the above-described parallel or serial digital embodiments may include signal processing that is programmed to ignore lower magnitude signals from adjacent sets and accept signals from all the remaining sets.

Skilled workers will recognize that portions of this invention may be implemented differently from the implementations described above for a preferred embodiment. For example, the invention may be adapted for use in counting particles in a liquid medium.

It will be obvious to those having skill in the art that many changes may be made to the details of the above-described embodiments of this invention without departing from the underlying principles thereof. The scope of the present invention should, therefore, be determined only by the following claims.

We claim:

1. An optical scattering method of determining a size of a particle, comprising:

injecting into a view volume having a longitudinal axis target particles having an injection velocity that varies as a function of a position along the longitudinal axis;

propagating coherent radiation having an intensity along the longitudinal axis of the view volume, the radiation exiting the view volume including an unscattered portion of the radiation unscattered by the target particles and a scattered portion of the radiation scattered by the target particles;

detecting with collection optics and an array of photo-detector elements the scattered portion of the radiation, each photo-detector element sensing radiation scattered from one of the positions along the longitudinal axis of the view volume and generating a signal having a magnitude that depends on the intensity of the radiation, the size of the target particle, and the injection velocity of the target particle; and adjusting a gain associated with each photo-detector element to compensate for the particle injection velocity variations along the longitudinal axis of the view volume so that a gain-adjusted magnitude of each signal represents substantially the size of the particle.

2. The method of claim 1 in which the intensity of the coherent radiation varies as a function of the position along the longitudinal axis and the adjusting further compensates for the intensity variations.

3. The method of claim 1 in which the array of photo-detector elements has a sensitivity that varies from element to element, and the adjusting further compensates for the sensitivity of each photo-detector element.

4. The method of claim 1 in which the collection optics have an associated radiation collection efficiency that varies as a function of the position along the longitudinal axis, and the adjusting further compensates for the associated radiation collection efficiency of the collection optics.

5. The method of claim 1 in which the injecting of target particles includes directing a flow stream of the target particles immersed in a gas carrier in a direction laterally across the coherent radiation propagating through the view volume.

6. The method of claim 1 in which the coherent radiation is produced by a diode-pumped solid-state laser.

7. The method of claim 1 in which the detecting further comprises mixing the scattered portion of the radiation and the unscattered portion of the radiation to provide a heterodyne detection of the target particles.

8. The method of claim 1 in which the signals are generated substantially concurrently and the adjusting is carried out in parallel.

9. The method of claim 1 in which the signals are generated sequentially and the adjusting is carried out by a gain normalization system.

10. The method of claim 1 in which the intensity of the coherent radiation has fluctuations and the method further includes sensing the intensity fluctuations and providing to a gain normalization system an intensity fluctuation signal that compensates for the intensity fluctuations so that the gain-adjusted magnitude of each signal represents substantially the size of the particle.

11. The method of claim 1 in which the size of the target particles is less than one micron.

12. The method of claim 1 further including summing the signals from adjacent pairs of the photo-detector elements to account for radiation scattered from a target particle that spans adjacent positions along the longitudinal axis of the view volume.

13. A method of improving a size determining accuracy of an optical particle detecting system, comprising:

injecting into a view volume having a longitudinal axis target particles having a predetermined size and an injection velocity that varies as a function of a position along the longitudinal axis;

propagating coherent radiation having an intensity along the longitudinal axis of the view volume, the radiation exiting the view volume including an unscattered portion of the radiation unscattered by the target particles and a scattered portion of the radiation scattered by the target particles;

detecting with an array of photo-detector elements the scattered portion of the radiation, each photo-detector element sensing radiation scattered from one of the positions along the longitudinal axis of the view volume and generating a signal having a magnitude that depends on the intensity of the radiation, the predetermined size of the target particle, and the injection velocity of the target particle; and adjusting a gain associated with each photo-detector element such that a gain adjusted magnitude of each signal is substantially equal thereby compensating for the particle injection velocity variations along the longitudinal axis of the view volume.

14. The method of claim 13 in which the intensity of the coherent radiation varies as a function of the position along the longitudinal axis and the adjusting further compensates for the intensity variations.

15. The method of claim 13 in which the array of photo-detector elements has a sensitivity that varies from element to element, and the adjusting further compensates for the sensitivity of each photo-detector element.

16. The method of claim 13 in which the array of photo-detector elements has an associated radiation collection efficiency that varies from element to element, and the adjusting further compensates for the associated radiation collection efficiency of each photo-detector element.

17. The method of claim 13 in which the introducing of target particles includes directing a flow stream of the target particles immersed in a gas carrier in a direction laterally across the coherent radiation propagating through the view volume.

18. The method of claim 13 in which the detecting further comprises mixing the scattered portion of the radiation and the unscattered portion of the radiation to provide a heterodyne detection of the target particles.

* * * * *